United States Patent [19]

Garbarg et al.

[11] Patent Number: 5,342,960
[45] Date of Patent: Aug. 30, 1994

[54] AZOMETHINES AGONIST COMPOUNDS OF THE HISTAMINE H3 RECEPTOR FOR THERAPEUTIC USE, PHARMACEUTICAL COMPOSITIONS ACTING AS AGONISTS OF THE SAID RECEPTOR AND PREPARATION PROCESS

[75] Inventors: Monique Garbarg, Paris; Jean-Michel Arrang, Gif sur Yvette, both of France; Walter Schunack, Berlin, Fed. Rep. of Germany; Ralph Lipp, Berlin, Fed. Rep. of Germany; Holger Stark, Berlin, Fed. Rep. of Germany; Jeanne-Marie Lecomte; Jean-Charles Schwartz, both of Paris, France

[73] Assignees: Institut National de la Sante et de la Recherche Medicale; Societe Civile Bioprojet, both of Paris, France

[21] Appl. No.: 828,936

[22] PCT Filed: May 10, 1991

[86] PCT No.: PCT/FR91/00384
§ 371 Date: Feb. 6, 1992
§ 102(e) Date: Feb. 6, 1992

[87] PCT Pub. No.: WO91/17146
PCT Pub. Date: Nov. 14, 1991

[30] Foreign Application Priority Data
May 9, 1990 [FR] France ................. 90 05776

[51] Int. Cl.⁵ ................. A61K 31/415; C07D 233/64; C07D 233/80
[52] U.S. Cl. .................................................. 548/336.1
[58] Field of Search ........................... 548/344, 336.1; 514/400

[56] References Cited

U.S. PATENT DOCUMENTS 4,558,062 12/1985 Kaplan .................. 514/400
4,767,778 8/1988 Arrang et al. ......... 514/397
5,034,539 7/1991 Arrange et al. ....... 548/344

FOREIGN PATENT DOCUMENTS 0024639 8/1980 European Pat. Off. .
0199407 10/1986 European Pat. Off. .

OTHER PUBLICATIONS

Chem. Abstr., 100, Jun. 1984, 209240f.
Chem. Abstr., 83, Jul. 1975, 3000z.
J. C. S. Chem. Comm., 1978, pp. 634–636.
J. Amer. Chem. Soc., Feb. 2, 1977, pp. 707–713.
J. Org. Chem., 48, 1983, pp. 2423, 2424.
Chem. & Pharm. Bull. 12, 1964, pp. 382, 383.
Chromatographia, 23, Sep. 1987, pp. 675–679.
J. Chem. Soc. C, No. 4, 1968, pp. 406–410.
J. Chem. Soc. C, No. 4, 1968, pp. 411–415.
Analytica Chimica Acta, 99, 1978, pp. 305–315.
J. Prot. Chem., 7, No. 5, 1988, pp. 549–559.
J. Org. Chem., 47, 1982, pp. 2663–2666.
Inorganica Chimica Acta, 67/85, No. 1, Jul. 1, 1982, pp. 71 ∝ 12.

(List continued on next page.)

Primary Examiner—Floyd D. Higel
Attorney, Agent, or Firm—Larson and Taylor

[57] ABSTRACT

Agonist compounds of the histamine H3 receptor for therapeutic use, pharmaceutical compositions acting as agonists of the said receptor and preparation process are disclosed.

The compounds are derived from an amine $R-NH_2$ having a high affinity for the histamine H3 receptor and to the primary amine function of which a group which gives rise to a bond that is capable of being slowly hydrolyzed in a neutral medium is attached. The pharmaceutical compositions contain these compounds and a pharmaceutically acceptable vehicle or excipient.

These compounds are used for producing a medicinal product which inhibits the synthesis and the release of histamine, in particular, possessing sedative, sleep-regulating, anticonvulsant, antidepressant, anti-allergic, anti-inflammatory, antisecretory or anti-ulcerous effects.

9 Claims, No Drawings

OTHER PUBLICATIONS

*J. Org. Chem.* vol. 31, No. 7, Jul. 1966, pp. 2380–2383.
*J. Amer. Chem. Soc.*, vol. 103, No. 21, 1981, pp. 6338–6347.
Chem. Abstr., vol. 95, Jul. 1981, 19963z.
*Liebigs Annalen der Chemie*, No. 2, Feb. 1982, pp. 254–264.
*J. Chem. Soc. C,* No. 22, 1966, pp. 2047–2051.
*Chimiko–Farmacevticeskij Zurnal,* vol. 21, No. 9, 1987, pp. 1034–1038.
*Lipids,* vol. 21, No. 1, 1986, pp. 6–10.
*Nature,* 1987, No. 327, pp. 117–123.
*Arc. Pharm.* (Weinheim), 1980, 313, pp. 709–714.
*Eur. J. Pharmacol.,* 1989, 164, pp. 1–11.
*J. Med. Chem.,* 1973, vol. 16, No. 6, pp. 616–620.
*Frontiers in Histamine Research,* Schunack, et al. Ganellin, et al., ed. Pergamon Press, 1985, pp. 39–46.
*J. Med. Chem.* 1976, vol. 19, No. 7, pp. 923–928.
*J. Med. Chem.,* 1970, 13, pp. 33–35.
*J. Chem. Soc.,* 1961, pp. 5037–5038.

AZOMETHINES AGONIST COMPOUNDS OF THE HISTAMINE H3 RECEPTOR FOR THERAPEUTIC USE, PHARMACEUTICAL COMPOSITIONS ACTING AS AGONISTS OF THE SAID RECEPTOR AND PREPARATION PROCESS

The present invention relates to compounds especially for therapeutic use as agonists of the histamine H3 receptor, to pharmaceutical compositions containing them and to the use of these compounds for producing a medicinal product.

The advantageous agonist properties with respect to the H3 histaminergic receptor of imidazolethylamine derivatives have been described in Patent Applications EP-A-0,214,058 and EP-A-0,338,939. These compounds are very potent in vitro since they act at nanomolar concentrations. They are also very active in vivo in rodents (rats or mice) in which they exert an inhibition of the synthesis and of the release of endogenous histamine from the brain and from various peripheral organs at doses close to 1 mg/kg: for example, the 50% effective dose of (R)-α-methylhistamine is 3 mg/kg orally (Arrang et al., Nature 1987, 327, 117–123; Garbarg et al., Eur. J. Pharmacol. 1989, 164, 1–11). This high activity in vivo is confirmed by the measurement of the plasma level of (R)-α-methylhistamine determined either by radioenzymatic assay (Garbarg et al., Eur. J. Pharmacol. 1989, 164, 1–11), or by a radioimmunoassay: at an oral dose of 3 mg/kg, plasma levels sufficient to stimulate the H3 receptor (>10 nM) are maintained for more than 6 hours.

However, by administering the same compound to a series of healthy volunteers at a dose of 175 mg per person, the Applicants observed that the plasma levels of (R)-α-methylhistamine which resulted from this administration were about 10 times lower than what was expected given the corresponding results obtained in rodents.

The Applicants have surprisingly discovered that by blocking the primary amine function of histamine derivatives, in particular among those described in the abovementioned European Patent Applications EP-A-0,214,058 and EP-A-0,338,939, compounds which are extremely active in vivo are obtained which are capable of being slowly hydrolyzed in a neutral medium to give the free derivative again. Similar results are obtained with all amines possessing a high affinity and selectivity for the histamine H3 receptor.

The subject of the invention is therefore a compound derived from an amine R-NH2, to the primary amine function of which a group which gives rise to a bond that is capable of being slowly hydrolyzed in a neutral medium is attached, R being such that the said amine possesses a high affinity for the histamine H3 receptor.

Compound is also understood as meaning the different isomeric forms as well as, where appropriate, the derivatives obtained by condensation of water as will be explained in greater detail later.

The amines R-NH2 to which the invention relates are more particularly the histamine derivatives, or more specifically the amines of the same chemical formula, described in the abovementioned Patent Applications EP-A-0,214,058 and EP-A-0,338,939, and which correspond to the formula:

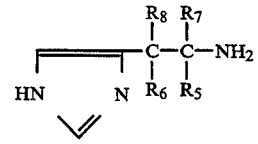

in which $R_5$, $R_6$ and $R_8$ each denote a hydrogen atom or a methyl group, or alternatively $R_5$ and $R_6$, taken together, form a methylene group and $R_7$ represents a hydrogen atom or a methyl or carboxyl group, $R_5$, $R_6$, $R_7$ and $R_8$ not being capable of simultaneously denoting hydrogen.

Among the amines which correspond to this formula, the following may be mentioned in particular:

1. α-Methylhistamine or 4-(2-aminopropyl)imidazole and more particularly its stereoisomer R(−); ($R_5$=CH$_3$; $R_6$=$R_7$=$R_8$=H); described by Gerhard and Schunack, Arc. Pharm. (Weinheim) 1980, 313, 709.
2. α,α-Dimethylhistamine or 4-(2-methyl-2-aminopropyl)imidazole ($R_5$=$R_7$=CH$_3$; $R_6$=$R_8$=H); described by Schunack, Joint Meeting of the American Chemical Society, Div. of Med. Chem., and the American Society for pharmacology and experimental therapeutic, Boston, USA, 18–22 August, 1985.
3. β-Methylhistamine or 4-(1-methyl-2-aminoethyl)imidazole and its stereoisomers ($R_6$=CH$_3$; $R_6$=$R_7$=$R_8$=H) described by Ganellin et al. in J. Med. Chem. 1973, 16, 616 (in racemic form) and by Schunack et al. in Frontiers in histamine research, C. R. Ganellin and J. C. Schwartz, ed. Pergamon Press, 1985, p. 39 (in the form of stereoisomers).
4. β,β-Dimethylhistamine or 4-(1,1-dimethyl-2-aminoethyl)imidazole ($R_5$=$R_7$=H; $R_6$=$R_8$=CH$_3$), described by Durant et al., J. Med. Chem. 1976, 19, 923.
5. 2-(4-Imidazolyl)cyclopropylamine ($R_5$=$R_6$=CH$_2$; $R_7$=$R_8$=H), described by Burger et al., J. Med. Chem. 1970, 13, 33.
6. α-Methylhistidine and its stereoisomers ($R_5$=CH$_3$; $R_7$=COOH; $R_6$=$R_8$=H), described by B. Robinson and T. M. Shepherd, J. Chem. Soc. 1961, 5037–8.
7. α,β-Dimethylhistamine and its stereoisomers ($R_5$=$R_8$=CH$_3$; $R_6$=$R_7$=H), described in EP-A-0,338,939.

According to the invention, the preferred amines are in particular (R)-α-methylhistamine, α,α-dimethylhistamine and α,β-dimethylhistamine.

According to the invention, the compound may comprise a ketone or aldehyde residue, in particular a cyclic ketone or aldehyde residue, attached to the primary amine function of the said amine.

According to the invention, the compound may advantageously correspond to the formula:

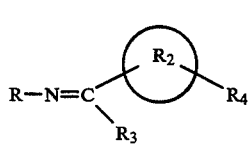

(1)

in which:

$R_2$ is a cyclic aryl or heteroaryl group optionally linked to $R_3$ and optionally mono- or polysubstituted with $R_4$, $R_3$ is H or any appropriate substituent or an aliphatic or an aromatic or non-aromatic cyclic chain, it being possible for $R_3$ to be in particular equal to $R_2$ or $R_4$, $R_4$ = any appropriate substituent such as H, OH, $CH_3$, $OR_3$, $COOR_3$, halogen, $CF_3$, alkyl (simple or substituted) and the like, and R-N is derived from the starting amine $R-NH_2$. Naturally, $R_2$ may be substituted at the same tithe by various substituents mentioned for $R_4$.

The subject of the present invention is more particularly a compound derived from histamine having a high affinity for the histamine $H_3$ receptor, characterized in that the said compound is obtained from a histamine derivative corresponding to the general formula

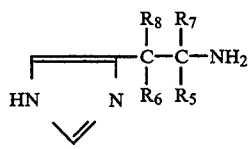
(2)

in which $R_5$, $R_6$ and $R_8$ each denote a hydrogen atom or a methyl group, or alternatively $R_5$ and $R_6$, taken together, form a methylene group and $R_7$ represents a hydrogen atom or a methyl or carboxyl group, $R_5$, $R_6$, $R_7$ and $R_8$ not being capable of simultaneously denoting hydrogen, to the primary amine function of which a group which gives rise to a bond that is capable of being slowly hydrolyzed in a neutral medium is attached.

The preferred compounds conforming to the invention are characterized in that they consist of azomethines corresponding to the general formula

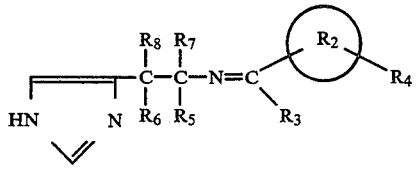
(3)

in which $R_5$, $R_6$, $R_7$ and $R_8$ have the meanings given above and $R_2$ is a cyclic aryl or heteroaryl group optionally attached to $R_3$ and optionally mono- or polysubstituted with $R_4$, $R_3$ is H or any appropriate substituent or an aliphatic or an aromatic or non-aromatic cyclic chain, it being possible for $R_3$ to be in particular equal to $R_2$ or $R_4$, $R_4$ = any appropriate substituent such as H, OH, $CH_3$, $OR_3$, $COOR_3$, halogen, $CF_3$, alkyl (simple or substituted), or of one or their salts such as, in particular, the hydrochlorides or maleates.

The chemical formulae which follow represent preferred compounds conforming to the invention, this list not being, of course, limiting:

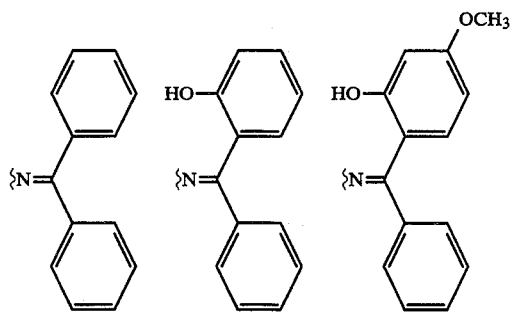

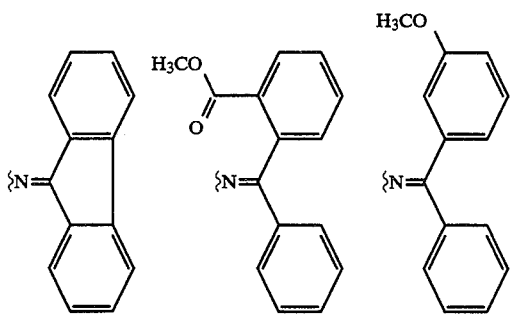

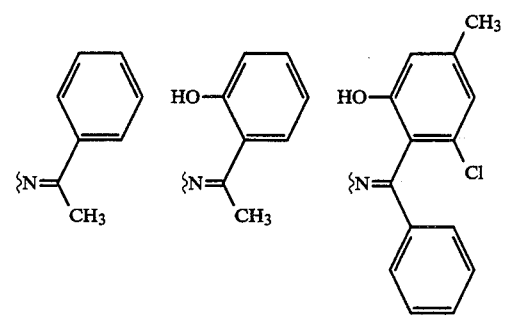

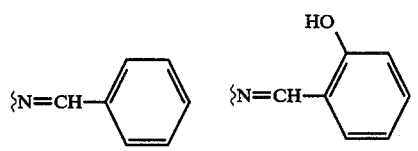

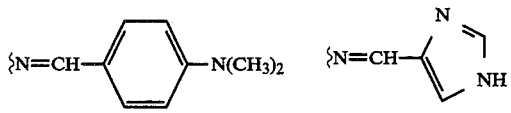

formulae in which N is the nitrogen atom of the primary amine function of the bound amine, the rest of whose molecule is not represented and which may be in particular one of the following two histamine derivatives:

(R)-α-methylhistamine

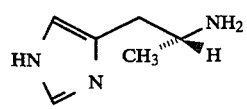

α,α-dimethylhistamine

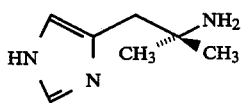

α,β-dimethylhistamine and, more particularly, its α-R, β-S isomer.

The compounds according to the invention are preferably produced by condensation of a free amine and a cyclic aldehyde or ketone, which should lead to a Schiff base which is capable of being slowly hydrolyzed in a neutral medium.

An example of synthesis is given below:

Preparation of
(R)-(−)-2-[N-[1-(1H-imidazol-4-yl)-2-propyl]-(iminophenylmethyl)]phenol (No. 94) from (R)-α-MeHA dihydromaleate 2.24 g (20 mmol) of potassium tert-butoxide are dissolved in 30 ml of anhydrous 2-propanol. After adding 1.79 g (5 mmol) of (R)-α-MeHA dihydromaleate, the suspension obtained is stirred overnight. The material which separates off (disodium maleate) is separated by filtration and washed twice with 5 ml of anhydrous 2-propanol. The combined filtrates are evaporated to dryness and redissolved in 40 ml of anhydrous ethanol. After adding 1.19 g (6 mmol) of 2-hydroxybenzophenone, the solution is refluxed for 15 min and evaporated to dryness. Diethyl ether and a few seed crystals are added to the oil obtained and the mixture is stirred for the crystallization. The yellow material obtained is recrystallized twice from cyclohexane/anhydrous ethyl acetate.

Yield 63.7% m.p.: 142°–144° C. (cyclohexane/EtOAc)

$C_{19}H_{19}N_3O$ (305.4) calculated C 74.73 H 6.27 N 13.76 found C 74.43 H 6.33 N 13.79.

$^1$H NMR: [D6]DMSO (300 MHz) δ=15.63 (s, replaceable by $D_2O$, 1H, Im-NH), 11.73 (br, replaceable by $D_2O$, 1H, OH), 5.51–6.54 (m, 11H, atom), 3.53 (dt, $J_1=J_2=6Hz$, 1H, CH—CH$_2$), 2.73 (d, J=6Hz, 2H, CH$_2$), 1.15 (d, J=6Hz, 3H, CH$_3$), ppm rel. TMS, MS: EI m/z (rel.int.[%]) 305 ([M]$^+$, 6), 224 (43), 172 (72), 171 (44), 144 (34), 118 (51), 89 (40), 69 (86), 41 (100).

IR: 3076 m, 2966 m, 2600 ns, 1961 s, 1606 s, 1571 cm$^{-1}$.

$[α]_D^{20} = -295.4°$ (MeOH, c=1).

In some cases the compound obtained may itself be recombined in the form of a derivative without losing its properties, in particular its ability to be hydrolyzed and to gradually release the starting amine, and a mixture of different forms of the relevant compound may be present.

The invention also relates to such derivatives and to mixtures of the various forms of the compound, as already mentioned above.

The following reaction illustrates this phenomenon in the case of (R)-α-methylhistamine:

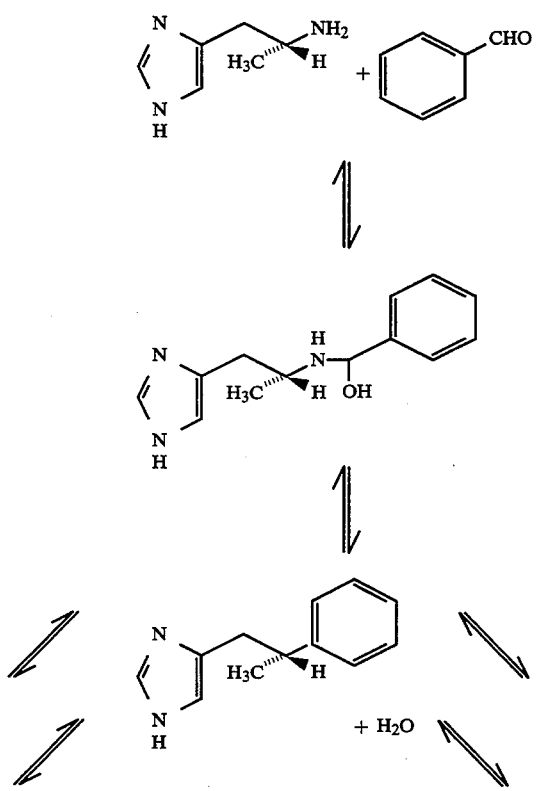

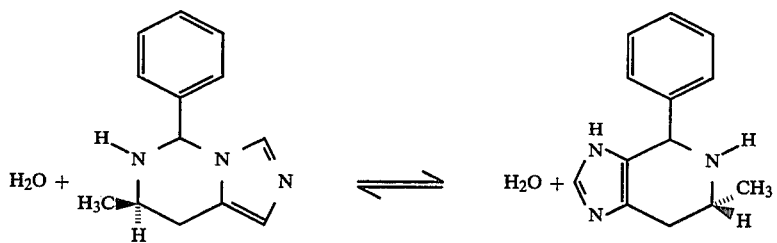

It is thought that the medicinal products or pharmaceutical compositions according to the invention act like a prodrug being slowly converted inside the organism to the biochemically active ingredient.

Another subject of the present invention is a pharmaceutical composition containing a compound according to the invention and a pharmaceutically acceptable vehicle or excipient.

Another subject of the invention is the use of a compound of formula (1) and, preferably, (2) or (3) for producing a medicinal product which inhibits the synthesis and the release of histamine or other $H_3$ receptor-regulated mediators, in particular, possessing sedative, sleep-regulating, anticonvulsant, antivertiginous, antidepressant, antiallergic, antiasthmatic, antipruriginous, anti-inflammatory (including in the gastrointestinal sphere), antisecretory or antiulcerous effects.

Other advantages of the invention will emerge from the description of the compounds according to the invention, taken as non-restrictive examples, and from trials carried out using these compounds.

The following compound I was produced by condensation of (R)-α-methylhistamine:

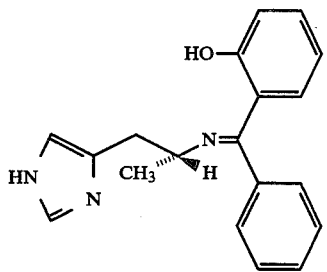

It has been found that:
1) the compound I is capable of being slowly hydrolyzed in vitro in a neutral medium (t ½>3 h at 25° C.) in the presence or in the absence of tissue extracts;
2) when administered orally to rodents, it is well absorbed as shown by the plasma levels determined by chemical hydrolysis followed by radioimmunoassays of the (R)-α-methylhistamine thus produced in vitro;
3) the compound I is well hydrolyzed in vivo in rodents because its administration leads to plasma (R)-α-methylhistamine levels which are at least equal to those produced by administering an identical molar dose of free amine; furthermore, these levels are maintained over a longer period and a more pronounced reduction in endogenous histamine synthesis (especially in the brain) results therefrom;
4) when administered to chimpanzees and to healthy human volunteers, the compound I leads to plasma (R)-α-methylhistamine levels 20 to 100 times higher than an equivalent molar dose of the free amine; furthermore, levels corresponding to an activation of $H_3$ receptors are maintained over a longer period because of the gradual hydrolysis of the compound I (the plasma level of which remains 5 to 10 times higher than that of the free amine).

Thus, the active doses in man by the oral route are, preferably, close to 1 to 20 mg instead of 100 to 300 mg for the free amine. A reduction in toxicity and side-effects and a reduction in the cost of preparing a unit dosage may be observed. Furthermore, the compound I is substantially more lipophilic than the free amine, which should facilitate the passage of membrane barriers such as the digestive or hemato-encephalic barriers and the access to the $H_3$ receptors which are nominally not very accessible to a free amine.

We claim:
1. A compound having the formula:

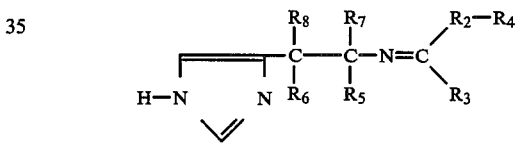

wherein
$R_5$, $R_6$, $R_7$ and $R_8$ each denote hydrogen or methyl, $R_5$ and $R_6$ taken together form methylene and $R_5$, $R_6$, $R_7$ and $R_8$ do not simultaneously denote hydrogen, $R_2$ is phenyl or imidazolyl, unsubstituted, monosubstituted or polysubstituted with $R_4$, and $R_2$ is unattached to $R_3$ or is attached to $R_3$, $R_3$ is H, or has the meaning of $R_2$ or $R_4$, and $R_4$ is H, $OR_3$, $COOR_3$, halogen, $CF_3$ or unsubstituted, monosubstituted or polysubstituted alkyl, or a pharmaceutically acceptable salt thereof.

2. A compound according to claim 1, wherein $R_2$ is phenyl unsubstituted or substituted with $R_4$ which represents hydroxyl, methoxy, halogen or COO—$CH_3$, and wherein $R_3$ represents phenyl.

3. A compound according to claim 1, wherein $R_2$ is phenyl unsubstituted or substituted with $R_4$ which represents hydroxyl, methyl, halogen or dimethylamino, and wherein $R_3$ represents hydrogen or methyl.

4. A compound according to claim 1, wherein $R_2$ is imidazolyl, and wherein $R_3$ and $R_4$ are each hydrogen.

5. A compound according to claim 1 wherein $R_5$ is $CH_3$ and $R_6$, $R_7$ and $R_8$ each is H.

6. A compound according to claim 1 wherein $R_5$ and $R_7$ each is $CH_3$ and $R_6$ and $R_8$ each is H.

7. A compound according to claim 1 wherein $R_5$ and $R_8$ each is $CH_3$ and $R_6$ and $R_7$ each is H.

8. A pharmaceutical composition containing the compound according to claim 1, and a pharmaceutically acceptable vehicle or excipient.

9. A pharmaceutical composition for inhibiting the synthesis and release of $H_3$ receptor-regulated mediators, comprising a compound having the formula

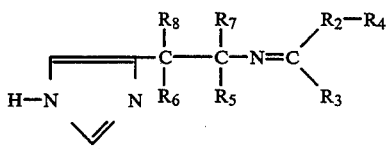

wherein
$R_5$, $R_6$, $R_7$ and $R_8$ each denote hydrogen, or methyl, $R_5$ and $R_6$ taken together form methylene and $R_5$, $R_6$, $R_7$ and $R_8$ do not simultaneously denote hydrogen,
$R_2$ is phenyl or imidazolyl, unsubstituted, monosubstituted or polysubstituted with $R_4$, and $R_2$ is unattached to $R_3$ or is attached to $R_3$,
$R_3$ is H, or has the meaning of $R_2$ or $R_4$, and
$R_4$ is H, $OR_3$, $COOR_3$, halogen, $CF_3$, or unsubstituted, monosubstituted or polysubstituted alkyl, or a pharmaceutically acceptable salt thereof.

* * * * *

UNITED STATES PATENT AND TRADEMARK OFFICE
CERTIFICATE OF CORRECTION

PATENT NO. : 5,342,960
DATED : Aug. 30, 1994
INVENTOR(S) : Garbarg, et al

It is certified that error appears in the above-indentified patent and that said Letters Patent is hereby corrected as shown below:

Column 6, last line, change the formula

"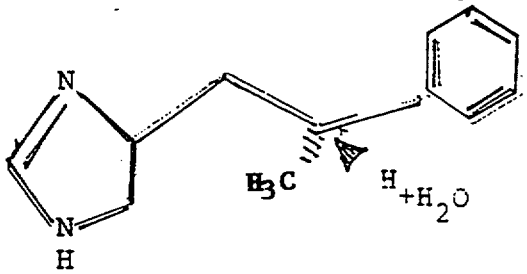"

to read as follows:

-- 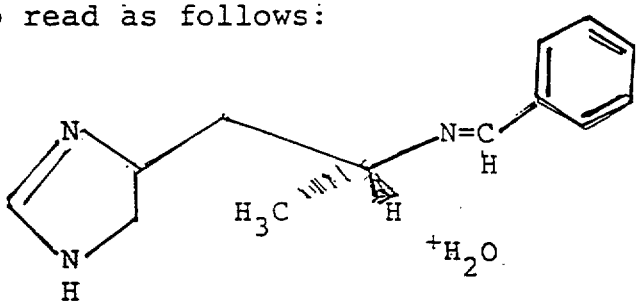 --

Signed and Sealed this

Twenty-third Day of July, 1996

Attest:

BRUCE LEHMAN

*Attesting Officer*   *Commissioner of Patents and Trademarks*